United States Patent [19]

De Boer et al.

[11] 4,040,533

[45] Aug. 9, 1977

[54] TRANSPORT DEVICE FOR TEST SAMPLE CARRIERS

[75] Inventors: Wilhelmus Johannes De Boer; Willem Schinkel, both of Almelo, Netherlands; Francis Johannes Span, Villebon-sur-Yvette, France

[73] Assignee: U.S. Philips Corporation, New York, N.Y.

[21] Appl. No.: 651,118

[22] Filed: Jan. 21, 1976

[30] Foreign Application Priority Data

Apr. 3, 1975 Netherlands .................... 7502498

[51] Int. Cl.² ............................................. B65G 65/04
[52] U.S. Cl. .................................. 214/310; 198/472; 198/656
[58] Field of Search ............... 214/300, 309, 310, 311, 214/16.1 CD; 198/85, 472, 580, 655, 656, 648, 339; 221/86

[56] References Cited

U.S. PATENT DOCUMENTS

| | | | |
|---|---|---|---|
| 3,221,781 | 12/1965 | Forsstrom | 198/85 |
| 3,561,004 | 2/1971 | Kozu et al. | 221/86 |
| 3,662,905 | 5/1972 | Mizuno et al. | 214/16.1 CD |
| 3,945,505 | 3/1976 | Frisbie et al. | 214/1 BB |

*Primary Examiner*—Lawrence J. Oresky
*Attorney, Agent, or Firm*—Frank R. Trifari; Rolf E. Schneider

[57] ABSTRACT

Apparatus for handling test-sample carriers in the form of elongate rectangular containers, each of which can accommodate a number of test-sample holders to be brought to a treatment station one after the other, comprises a rectangular table having two adjacently situated longitudinally extending zones each provided with a pair of parallel longitudinally extending conveyor belts respectively movable in opposite directions. The containers loosely rest in a transverse position on such belts by means of protrusions provided on their undersides. At the end of each zone, a stop is provided for arresting the containers. For the transverse displacement of the containers, on each end of the table there is provided a pin or roller which is eccentrically connected to a rotatable shaft such that the pin or roller can perform a rotary movement in the plane of the sidewall of a container bearing against the stop and which cooperates with slot-shaped recesses provided in the relevant sidewall of each container.

3 Claims, 5 Drawing Figures

TRANSPORT DEVICE FOR TEST SAMPLE CARRIERS

This invention relates to a transport device for test sample carriers in the form of elongate rectangular containers, each of which is capable of containing a number of test sample holders which are to be brought to a treatment station one after the other, such device comprising a rectangular table provided with a pair of adjacently situated longitudinally extending zones wherein the containers are displaced in opposite longitudinal directions by transport means, means being provided at each end of the table, viewed in the direction of movement of the containers, for the transverse displacement of the containers from one zone to the other zone.

A transport device of the kind set forth is known from U.S. Pat. No. 3,221,781. In this known device, the transport means are arranged only at the beginning of each of the zones, these means longitudinally advancing the container situated at the front in the relevant zone over one container width. Therefore, so as to ensure a regular and stepwise longitudinal advance of all the containers in this device both zones must always be completely filled with containers. This, of course, substantially restricts the possibilities of use of the device. For example, it is impossible to pass a limited number of containers through the device quickly.

The invention has for its object to eliminate this drawback. The transport device according to the invention is characterized in that the transport means are formed by at least two comparatively narrow and parallel conveyor belts in each zone, on which belts the containers rest by means of protrusions provided on their undersides, one or more stops being provided at the end of each of the zones, viewed in the direction of movement of the belts, for arresting the containers. In the device according to the invention, a container can be placed on the conveyor belts at any desired instant. This container is immediately taken along by the moving belts until the container abuts the stops in the case of a completely empty zone, or until the container abuts the last one of a number of containers still present in the zone.

The container subsequently remains stationary, the conveyor belts then sliding underneath the containers. The container arrested by the stops is displaced in a stepwise manner in the transverse direction to the adjacent zone, a treatment station arranged in the path of this displacement being passed during the displacement. The containers not yet contacting the stops await their turn, without special supervision or control devices being required.

The transverse displacement in a preferred embodiment according to the invention is effected by a pin or roller which is provided at each end of the table and which is eccentrically connected to a rotatable shaft which is coupled to a drive such that the pin or roller can perform a rotary movement in the plane wherein the sidewall of a container contacting the stops is situated, the pin or roller co-operating with slot-shaped recesses which are provided in the relevant side wall of each container and which are open at at least one end. The pin or roller thus co-operates with the slots in the side walls of the container to be transported in the manner of Maltese cross transmission, each revolution of the pin or roller advancing the container one step. The protrusions underneath the container then disengage from the conveyor belts, so that the container cannot occupy an inclined position on the belt. In the other zone the protrusions contact the conveyor belts only during the last step, after which further transport in the relevant zone can commence.

A difficulty encountered in the transport of test sample holders, usually bottles, in containers is the fact that the test sample holders must somehow be transferred from the container to a detection device at the treatment station. According to the invention, this problem is solved in that the containers are provided with compartments which are provided on the lower inner surface with a pair of resilient lugs against which the holders bear and which can be moved apart, after which the holders can drop from the compartments so as to be transported to the station. For moving these lugs apart, a further preferred embodiment of the transport device according to the invention is characterized in that a raised portion is provided between the zones on at least one end of the table, in the path of the transverse displacement of the containers, such raised portion having an opening for the passage of a test sample holder to a treatment station and having a slightly outwardly beveled front and rear, viewed in the direction of movement of the containers, such that the resilient lugs which are present in the containers and against which the sample holders bear can be moved apart by the raised portion.

The invention furthermore relates to a test sample carrier in the form of an elongate rectangular container for use in the described transport device. The shape and the advantages of this container, which may be completely made of a synthetic material according to the invention, have already been indicated in the foregoing and will be described in detail with reference to the drawings, in which:

FIG. 1 diagrammatically shows (not to scale) a transport device on which a number of container-shaped test sample carriers are arranged.

Figure 1:
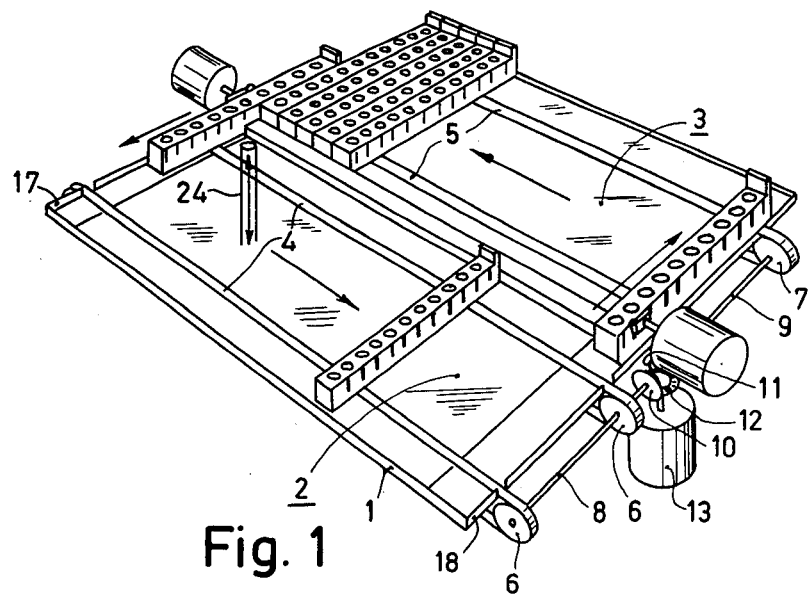

The reference 1 in FIG. 1 denotes a rectangular table. This table comprises two adjacent longitudinally extending zones 2 and 3, in each of which a pair of parallel longitudinally extending conveyor belts 4 and 5 is arranged. The conveyor belts 4 are guided over cooperating rollers 6 which are arranged on both ends of the table 1, the conveyor belts 5 being guided in a corresponding manner over rollers 7. On the one end of the table, the rollers 6, 7 are connected by shafts 8, 9 respectively, which carry beveled gearwheels 10 and 11 respectively, on their ends which are adjacent one another, such gearwheels co-operating with a common beveled gearwheel 12 which is mounted on the shaft of an electric motor 13. As a result of this coupling, when the electric motor 13 rotates, the conveyor belts 4 will start to move in the one longitudinal direction (for example, as denoted by the arrow) and the conveyor belts 5 will move in the opposite longitudinal direction.

Figure 2:
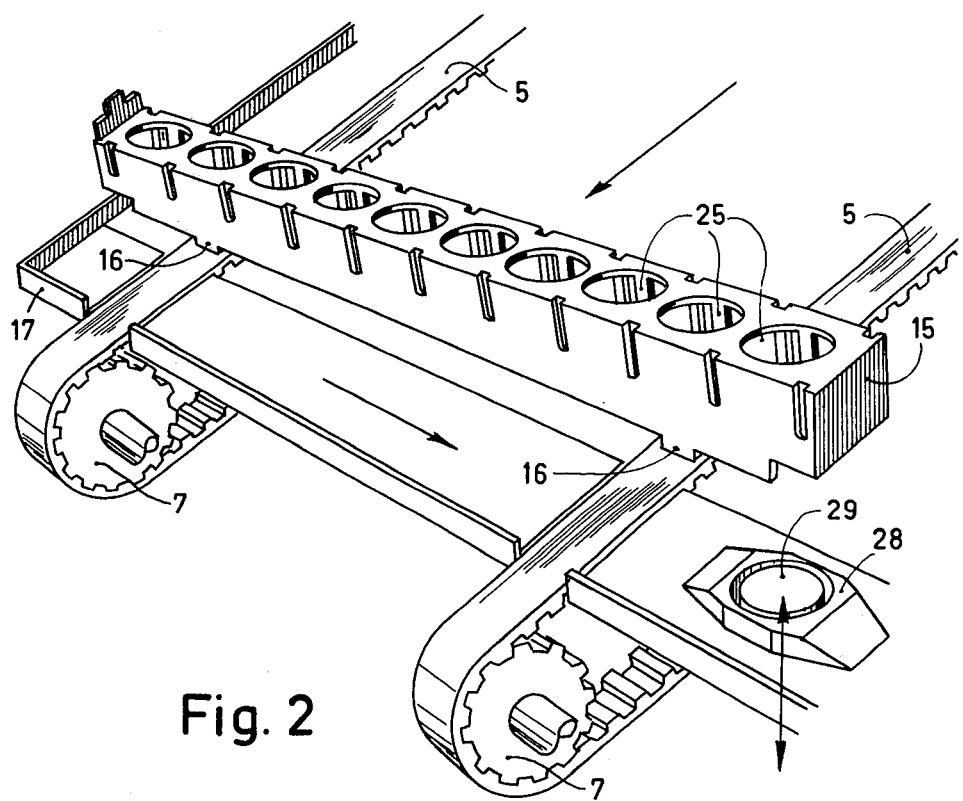
FIG. 2 shows a portion of FIG. 1 on an enlarged scale.
Figure 3:
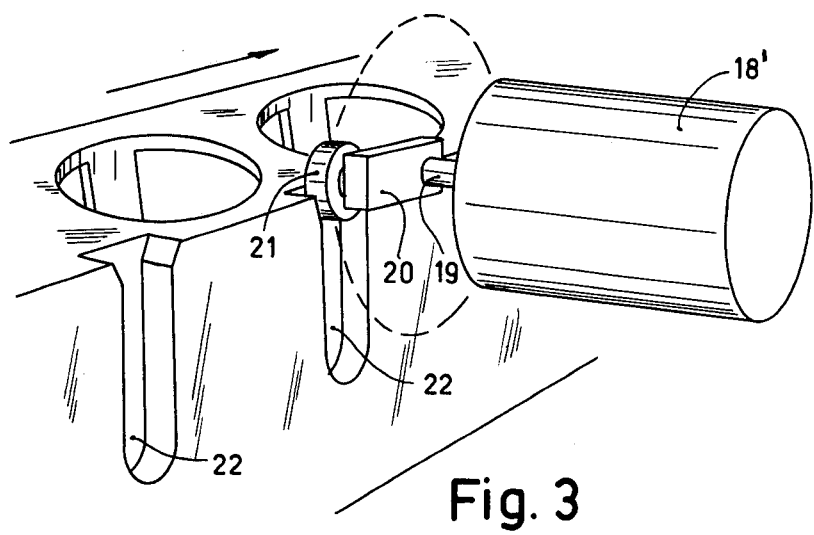
FIG. 3 shows a portion of the transverse displacement mechanism for the containers.

On the conveyor belts 4 and 5 a number of container-shaped test sample carriers 15 can be respectively arranged. These carriers or containers 15 rest on the conveyor belts by means of protrusions 16 (FIG. 2) provided on their undersides. The conveyor belts 5 move the containers 15, until the most forward one abuts a stop 17 provided at one end of the table (a stop 18 is provided at the other end of the table). The number of containers present in a zone is of no importance, because the containers continue to move with the conveyor belts until they either abut the relevant stop or the preceding container. The movement of the containers is then stopped, and the conveyor belts slide underneath the containers. Such operation ensures that the container to be transported in the transverse direction has indeed arrived in the correct position.

At each end of the table there is arranged an electric motor 18', the shaft 19 of which supports a roller 21 via a crank 20. This roller 21 performs a circular motion when the shaft 19 rotates. The roller 21 is arranged so that it performs its circular motion in a plane which at least substantially coincides with the plane containing the side wall of a container that abuts the stop 17 or 18. In the side walls of the containers slot-shaped recesses 22 are provided, having a transverse dimension which approximately corresponds to the diameter of the roller 21.

As a result of these provisions, upon each revolution of the shaft 19 the container 15 will be sequentially displaced, in the manner of a Maltese cross transmission, over one step transversely of the direction of movement of the conveyor belts. Due to this stepwise transverse displacement, the containers 15 move from zone 3 to zone 2, or at the other end of the table from zone 2 to zone 3. By suitable programming of the motor 18', the intervals between the steps can be adjusted as desired.

Figure 4:
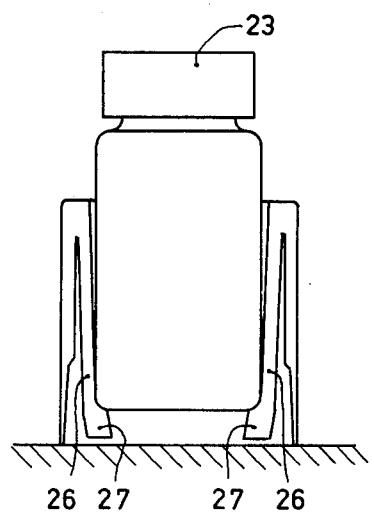
FIG. 4 is a cross-sectional view of a container containing a test sample holder.

These intervals are used for transferring the test sample holders 23 (FIGS. 4, 5) from the containers 15 to a detection device. The detection device is not shown in FIG. 1, but a transfer mechanism 24 is shown diagrammatically. This mechanism is situated underneath the table 1 and moves the holders 23 downwards through the bottom of the containers 15. In order to realize this, the containers 15 are provided with a number of compartments 25, in each of which fits a test sample holder 23. The walls of each of the compartments are at least partly formed by two oppositely disposed resilient lugs 26, the lower ends of which are provided with inwardly projecting portions 27 whereon the test sample holders rest. The entire container, including the resilient lugs, can be made of a synthetic material as an integral unit.

In order to permit the removal of the test sample holders 23 in the downward direction at the appropriate instant, a raised portion 28 is provided above the transfer mechanism 24 in the path travelled by the containers 15 during their transverse displacement from zone 3 to zone 2. This raised portion 28 surrounds an opening 29 through which can pass the transfer mechanism 24 and a test sample holder.

Figure 5:
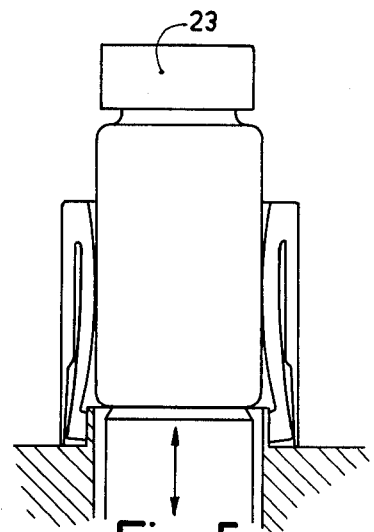
FIG. 5 is the same cross-sectional view as FIG. 4, but now in a situation where the relevant compartment is situated over the treatment station.

The raised portion 28 is beveled slightly outwardly on its front and rear so that, when a container 15 slides over the raised portion 28, the resilient lugs 27 are forced apart by the raised portion 28, with the result that the test sample holder 23 can be removed from the compartment 25 in the downward direction (FIG. 5).

What is claimed is:

1. Test-sample handling apparatus comprising elongate rectangular test-sample containers each having a plurality of open-ended compartments respectively adapted to receive test-sample holders to be brought to a treatment station one after the other, a rectangular table having two adjacently situated longitudinally extending zones, a pair of parallel longitudinally extending conveyor belts arranged in each zone, said containers being transversely positionable on said belts and having protrusions on their undersides for resting on said belts, means to continuously move said respective pairs of conveyor belts in opposite directions, a stop provided at the end of each zone toward which the containers are moved by the conveyor belts, means at the respective ends of the table for transversely displacing a container from one zone to the other in a step-wise manner, at least one of the table ends being associated with a treatment station over which each container is passed during its step-wise transverse displacement and means at said treatment station for ejecting each successive test-sample holder free of the test-sample container which carries said holder.

2. Apparatus according to claim 1, in which each sidewall of a container is provided with a plurality of equally spaced slot-shaped recesses open at one end, and in which the transverse displacement means comprises a pin or a roller eccentrically mounted on a rotatable shaft such that rotary movement of the pin or roller occurs in the plane wherein the corresponding sidewall of a container is situated, the pin or roller cooperating with the recesses in said sidewall to effect the step-wise transverse displacement of said container.

3. Apparatus according to claim 1, in which the inner surface of each compartment is provided with resilient lugs adapted to press against a test-sample holder therein, and in which the end of the table associated with the treatment station is provided with a raised portion having an opening for passage of a test-sample holder to the treatment station, said raised portion having an outwardly beveled front and rear, viewed in the transverse direction of movement of the containers, whereby such raised portion spreads apart the resilient lugs in a compartment passing thereover to permit a test-sample holder in such compartment to drop through said opening.

* * * * *